US009022784B2

(12) United States Patent
Johansson et al.

(10) Patent No.: US 9,022,784 B2
(45) Date of Patent: May 5, 2015

(54) DENTAL BRIDGES AND SUPERSTRUCTURES, AND METHODS FOR MANUFACTURING THEREOF

(75) Inventors: Martin Johansson, Helsingborg (SE); Kristofer Frick, Helsingborg (SE); Anders Falk, Helsingborg (SE); Kristofer Svensson, Sosdala (SE)

(73) Assignee: Heraeus Kulzer Nordic AB, Helsingborg (SE)

( * ) Notice: Subject to any disclaimer, the term of this patent is extended or adjusted under 35 U.S.C. 154(b) by 0 days.

(21) Appl. No.: 13/883,664

(22) PCT Filed: Nov. 4, 2011

(86) PCT No.: PCT/SE2011/051315
§ 371 (c)(1),
(2), (4) Date: Dec. 18, 2013

(87) PCT Pub. No.: WO2012/064257
PCT Pub. Date: May 18, 2012

(65) Prior Publication Data
US 2014/0113248 A1    Apr. 24, 2014

Related U.S. Application Data

(60) Provisional application No. 61/417,354, filed on Nov. 26, 2010.

(30) Foreign Application Priority Data

Nov. 10, 2010  (SE) ........................ 1051181

(51) Int. Cl.
*A61C 13/12* (2006.01)
*A61C 13/00* (2006.01)
(Continued)

(52) U.S. Cl.
CPC ......... *A61C 13/0018* (2013.01); *A61C 13/0004* (2013.01); *A61C 13/0006* (2013.01); *A61C 13/0019* (2013.01); *A61C 13/0022* (2013.01); *A61C 8/0068* (2013.01); *A61C 13/04* (2013.01)

(58) Field of Classification Search
CPC ...... A61C 8/005; A61C 8/006; A61C 8/0066; A61C 8/0089; A61C 13/01; A61C 13/04; A61C 13/0004; A61C 13/0006; A61C 13/0022; A61C 13/081; A61C 13/2255; A61K 6/0225
USPC ........................... 433/172–176, 199.1, 200.1
See application file for complete search history.

(56) References Cited

U.S. PATENT DOCUMENTS

| 5,257,460 A | 11/1993 | McMurtry |
| 7,112,064 B1 * | 9/2006 | Fenc ............................ 433/185 |

(Continued)

FOREIGN PATENT DOCUMENTS

| EP | 1 505 041 | 2/2005 |
| EP | 2014254 | 1/2009 |

(Continued)

OTHER PUBLICATIONS

International Search Report and Written Opinion for International Application No. PCT/SE2011/051315 mailed Dec. 22, 2011.

(Continued)

*Primary Examiner* — Cris L Rodriguez
*Assistant Examiner* — Matthew Saunders
(74) *Attorney, Agent, or Firm* — Merchant & Gould P.C.

(57) ABSTRACT

The present disclosure provides a dental bridge intermediary structure (20) comprising a superstructure (200) and a connection piece (210), as well as connection piece for a dental bridge intermediary structure (20). A method for producing a dental bridge superstructure (200) is also provided.

7 Claims, 3 Drawing Sheets

(51) Int. Cl.
*A61C 8/00* (2006.01)
*A61C 13/01* (2006.01)

(56) References Cited

U.S. PATENT DOCUMENTS

| | | | |
|---|---|---|---|
| 2008/0241794 A1 | 10/2008 | Urata et al. | |
| 2008/0241798 A1 | 10/2008 | Holzner et al. | |
| 2010/0143868 A1 | 6/2010 | Hintersehr | |
| 2010/0323327 A1* | 12/2010 | Eriksson et al. | 433/199.1 |

FOREIGN PATENT DOCUMENTS

| | | |
|---|---|---|
| EP | 2 246 008 | 11/2010 |
| WO | WO 92/22785 | 12/1992 |
| WO | WO 2005/077296 | 8/2005 |
| WO | WO 2006/079188 | 8/2006 |
| WO | WO 2008/148495 | 12/2008 |
| WO | WO 2009/068559 | 6/2009 |
| WO | WO 2010/094922 | 8/2010 |

OTHER PUBLICATIONS

Albert. "This Golf Ball Mold is Really Cool." *Modern Machine Shop Blog* http://www.mmsonline.com/blog/post/this-golf-ball-mold-is-really-cool (Sep. 24, 2010).

Beard. "Under Control." *Modern Machine Shop Blog* http://www.mmsonline.com/articles/under-control (May 15, 1999).

Buckingham. "Industrial Tooling 1997: Artefact comparison techniques for achieving traceable measurement on CNC machine tools" Gloucestershire, UK (1997) 7 pages.

Ceng et al. "Quick Change Tooling for Flexible Machining:—Process Control—the contribution of touch trigger probing." *One Day Seminar and Exhibition in Coventry*, West Midlands. UK. Apr. 1989. 7 pages.

Kruth et al. "Rapid Manufacturing of Dental Prostheses by means of Selective Laser Sintering/Melting." *Proceeding of the AFPR.* (2005) 9 pages.

Kruth et al. "Rapid Manufacturing of Dental Prostheses by means of Selective Laser Sintering/Melting." *Proceeding of the AFPR.* (2005) 2 pages.

Lai et al. "A Flexible Rapid Prototyping Cell." *Solid Freeform Fabrication Symposium*, Austin, TX. (2000). pp. 275-282.

Lynch. "Key CNC Concept #4—The Forms of Compensation." *Modern Machine Shop Blog.* http://www.mmsonline.com/articles/key-cnc-concept-4$^{th}$-forms-of-comparison (Apr. 1, 1997).

Qu et al. "STL-based Finish Machining of Rapid Manufactured Parts and Tools." *Solid Freefrom Fabrication Symposium*, Austin, TX. (2001) pp. 304-312.

Shi et al. "Surface Finishing of Selective Laser Sintering Parts with Robot." *Solid Freefrom Fabriciation Symposium*, Austin, TX. (1998), pp. 27-36.

Unknown. "[IMTS Preview] AgiCharmilles to Demo Start-to-Finish Manufacturing for Mold Tooling." *American Machinist.* (Aug. 31, 2010).

Unknown. "GF AgieChannilles and EOS Partner to Pioneer Toolmaking Process." *Prototype Today*. http://www.prototypetoday.com (Sep. 4, 2013).

Zelinski. "How to Perfect a Machining Process (or at Least how to Make it More Trustworthy)." *Modern Machine Shop Blog* http://www.mmsonline.com/articles/how-to-perfect-a-machining-proces-or-atleast-how-to-make-it-more-trustworthy (Feb. 4, 2005).

Chinese Office Action for corresponding application No. 201180054365.7 mailed Nov. 21, 2014 (10 pages).

* cited by examiner

DENTAL BRIDGES AND SUPERSTRUCTURES, AND METHODS FOR MANUFACTURING THEREOF This application is a National Stage Application of PCT/SE2011/051315, filed 4 Nov. 2011, which claims benefit of Serial No. 1051181-4, filed 10 Nov. 2010 in Sweden and Ser. No. 61/417,354, filed 26 Nov. 2010 in the United States and which applications are incorporated herein by reference. To the extent appropriate, a claim of priority is made to each of the above disclosed applications.

FIELD OF THE INVENTION

This invention pertains in general to the field of an implant arrangement, and in particular to a dental bridge intermediary structure and more particularly to a dental bridge superstructure.

BACKGROUND OF THE INVENTION

In the field of dental implant technology, Cobalt Chrome (CoCr) is a commonly used material. Dental technicians usually cast dental bridge superstructures of CoCr and subsequently burn porcelain surfaces onto them to obtain a dental prosthesis, which may be attached to dental implants in the jaw. However, the casting process is cumbersome as it requires much preparation with moulds, and the precision in the obtained products is relatively low.

An alternate method for producing a superstructure is to mill/cut a raw material, such as a cuboid or cylinder, made of a suitable material, such as CoCr, into the desired shape. However, this technology gives rise to large amount of material spill, and due to the strength of the material, the milling/cutting is very time consuming and the wear on milling/cutting tools is high.

Also, there is a problem in the field regarding the ability to treat superstructures and dental bridges in subsequent treating stations, to improve adaptation between the superstructure or dental bridge and the structure to which it is intended to be attached, since translation between for example different kind of cutters is lacking.

US 2008/241798 discloses a system for sintering a superstructure for cementing onto polished tooth or implant support structures, wherein the sintering step is followed by a cutting step, for creating a smooth inner area in the cavity to be applied onto the polished tooth or implant support structure. The internal preparation line is made smooth to facilitate cooperation with the polished tooth or support structure, and to avoid bacterial attacks, being more prone in uneven surfaces.

Hence, an improved method for producing dental prostheses would be advantageous and in particular a method allowing for increased flexibility, cost-effectiveness or user friendliness as well as translation between different machineries would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a dental bridge intermediary structure, a connector, a method and a superstructure.

In a first aspect, a dental bridge intermediary structure is provided, comprising a superstructure with seats for connection to dental implants and a connection piece, wherein the connection piece comprises connection means for connecting the dental bridge intermediary structure to a cutter, and reference means for positioning of the superstructure in the cutter.

In a second aspect, a mill/cutter reference piece for a dental bridge intermediary structure according to the first aspect is provided, comprising a positioning portion and a fastening portion, wherein the positioning portion comprises complimentary connection means for interaction with the connection means of a dental bridge intermediary structure, and complimentary reference means for interaction with the reference means of a dental bridge intermediary structure.

In a third aspect, a method for producing a dental bridge superstructure is provided, comprising the steps of
 shaping a dental bridge intermediary structure comprising a superstructure and a connection piece, wherein the connection piece comprises connection means for connecting the dental bridge intermediary structure to a cutter, and reference means for positioning of the superstructure in the cutter;
 connecting the connection piece to the cutter; and
 cutting the seats for connection to the dental implants of the dental bridge intermediary structure with the cutter.

In a fourth aspect, a dental bridge superstructure, obtainable by a method according to the third aspect is provided.

In a fifth aspect the dental bridge superstructure further comprises screw channels for screw retaining the superstructure to the dental implants, wherein screw member seats are located in the bottom of the screw channels, such that screw members may be inserted through a first mouth of the screw channels, respectively, and screwed into the dental implants by receiving the threaded parts of the screw members through mouths of the screw member seats. The screw channels may be straight or bent/angled if it is preferred to position the first mouths on the buccal side of the superstructure.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on an embodiment of the present invention applicable to a dental prosthesis, such as a dental bridge superstructure, with seats for connection to dental implants. However, it is provided that the method may be used for producing all kinds of small scale prostheses.

Figure 1:
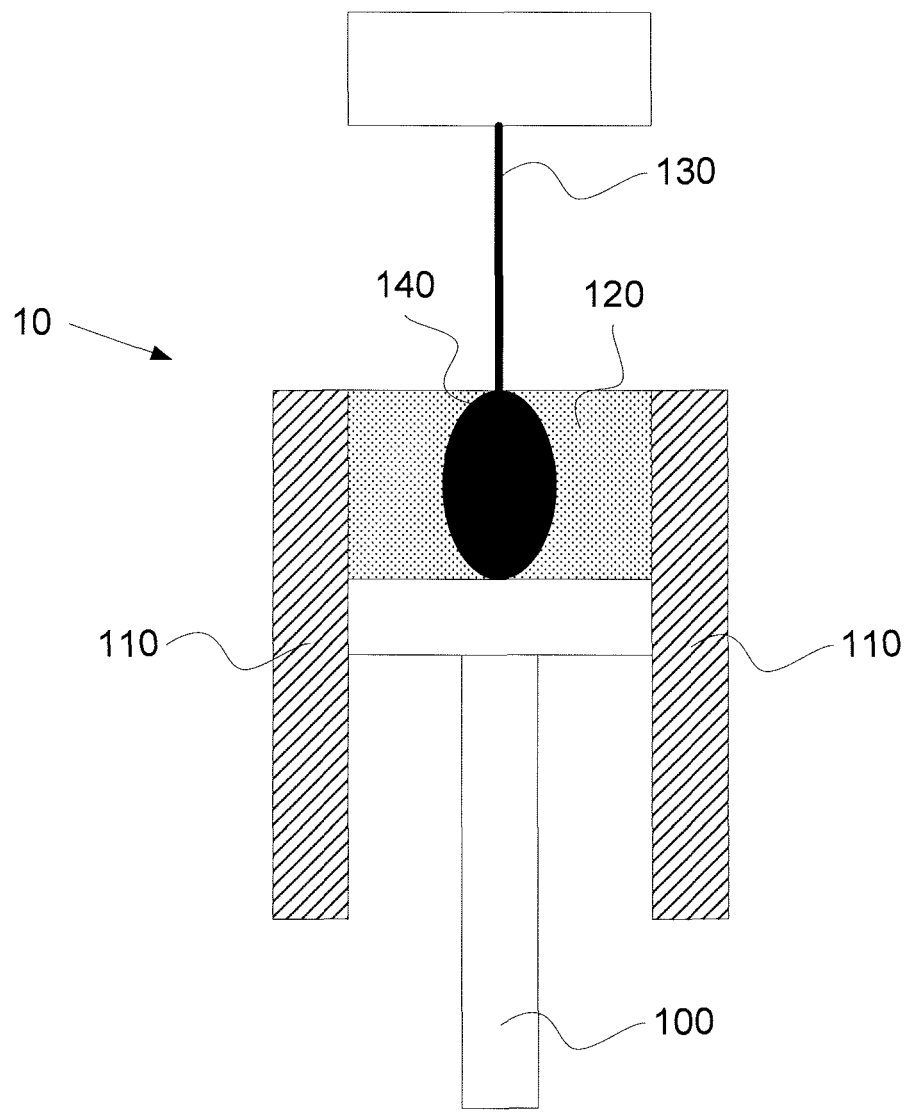
FIG. 1 is an illustration of an instrumental setup for laser sintering according to an embodiment.

Sintering, such as laser sintering, is a method for shaping a three dimensional structure by fusing small particles for example by means of a high power laser. FIG. 1 is a schematic illustration of an instrumental setup for laser sintering. A piston 100 is movably placed in a surrounding structure 110 so that a space is formed with the surrounding structure 110 as walls and the piston 100 as bottom. Small particles of the desired material 120 are added to the space from the top and a movable laser beam 130 is sintering a desired portion of the top layer of the particles into a solid structure. Next, the piston is moved downwards and more material 120 is added on top of the already sintered structure before another run by the movable laser beam 130. By repeating the process, a three dimensional structure 140 is created.

The sintering process is considered not sufficiently precise to use for manufacturing of a dental bridge superstructures. This is due to the fact that the sintering process generates a large amount of heat, which warps the sintered products when they cool. This is considered especially problematic in the field of the manufacturing of dental superstructures for direct interaction with dental implants on a fixture level, since the seats for attachment to dental implants are extremely sensitive to lacking preciseness. It is even more problematic with regard to superstructures intended for screw retention to dental implants, since then the screw member seat mouth has to be positioned exactly over and in correlation with the female threaded part of the dental implant, such that the screw member may be safely inserted through the screw channel and passing its threaded part through the mouth of the screw member seat to secure the superstructure to the dental implants through interaction between the threaded screw member male part and the threaded dental implant female part. This, singly or in combination with the fact that the surface of the sintered three dimensional structure 140 is not fine or smooth enough for a dental bridge superstructure, has led the skilled person away from manufacturing dental superstructures by sintering, such as laser sintering. Also, the warping of the superstructure during and after sintering would displace the direction of the screw member seat mouth if the screw channel is formed during the sintering step. Additionally, if the screw channel was formed during sintering, and not during milling subsequent to sintering, the warping during cooling of the sintered product could jeopardize the form of the screw channel, such that a screw member not would be allowed to reach or cooperate with the screw member seat at the bottom of the screw channel. For example the warping distortion could bend or re-shape the screw channel into an angle or shape that no longer allow the screw member to be inserted in the screw channel.

However, by combining sintering with subsequent cutting or milling of the dental implant seats and preferably the screw channels, it is possible to conveniently build a three dimensional structure with a smooth surface, without the excess spill from the cutting process, and with improved precision, i.e. high level of detail, while further obtaining exact cooperation between the dental implant female part and the direction of the screw member seat mouth, such that the screw member freely may be brought into retaining cooperation with the dental implant through the screw channel. It is however difficult to establish and translate the coordinates of the specific parts of the dental bridge superstructure, when moving the product from the sintering step to the cutting or milling step, due to warping of the dental bridge superstructure during sintering. Thus, the boundaries or edges of the sintered superstructure may not exactly correspond to the drawing, which makes it hard to position the superstructure for subsequent cutting, based on these boundaries.

Figure 2:
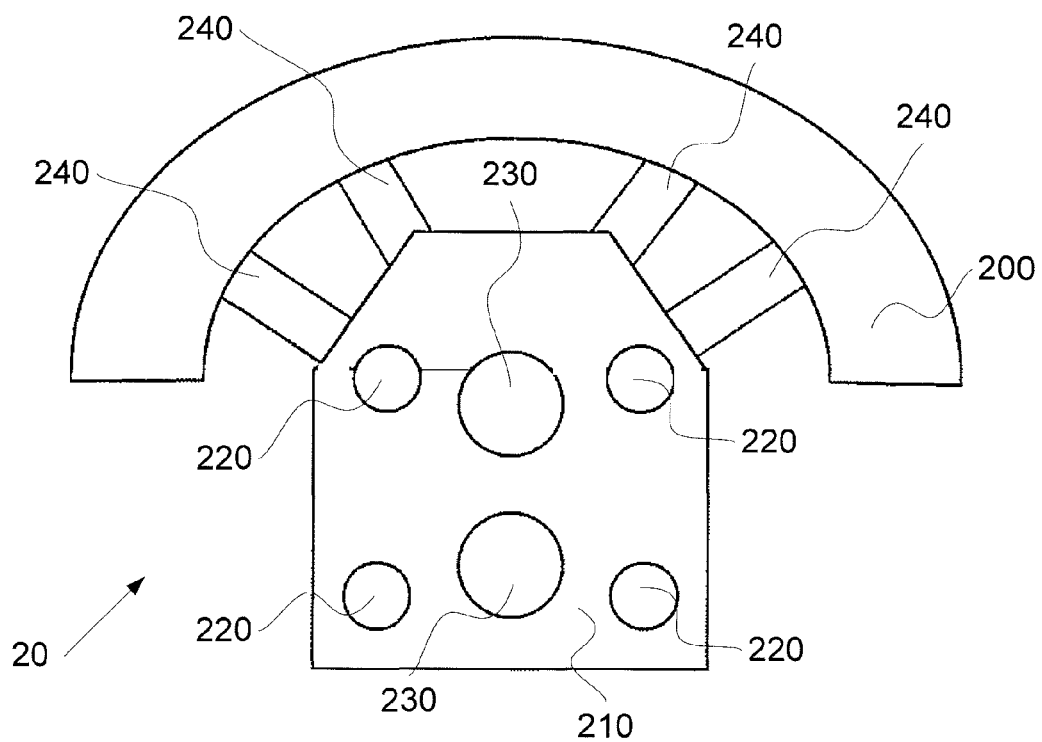
FIG. 2 is an illustration of a dental bridge intermediary structure according to an embodiment.

According to one embodiment of the present invention a dental bridge intermediary structure 20, according to FIG. 2, is therefore provided. The dental bridge intermediary structure 20 comprises a superstructure 200 and a connection piece 210. The connection piece 210 comprises connection means 220 for connecting the dental bridge intermediary structure 20 to a cutter, and reference means 230 for positioning of the superstructure 200 in the cutter. The reference means 230 and the connection means 220 may be the same structural unit, which will be further disclosed below.

In a specific embodiment, the connection piece 210 is a plate which is sintered in the same process, i.e. sintering step, as the superstructure 200, in the same piece as the superstructure. In this way, the superstructure 200 is obtained with integrated connection piece 210. The connection piece 210 is thus homogenous with the superstructure 200. A first advantage with this connection piece 210 is that the connection piece 210 stabilizes the superstructure 200 during sintering, to prevent or counteract warping of the superstructure 200. A second advantage of this connection piece 210 is that the connection piece may translate or transfer the coordinates of the superstructure 200 from the sintering step to the milling/cutting step.

The dental bridge intermediary structure 20 may then be made by Cobalt Chromium (CoCr), through a sintering process, such as laser sintering, which will be described below.

In a specific embodiment, the connection piece 210 is a plate which is milled/cut in the same process, i.e. milling step, as the superstructure 200, in the same piece as the superstructure, from the same blank. In this way, the superstructure 200 is obtained with integrated connection piece 210. The connection piece 210 is thus homogenous with the superstructure 200. A first advantage with this connection piece 210 is that the connection piece 210 stabilizes the superstructure 200 during milling, to prevent or counteract warping of the superstructure 200. A second advantage of this connection piece 210 is that the connection piece may translate or transfer the coordinates of the superstructure 200 from the milling step, substantially for producing the dental bridge intermediary structure 20, to a subsequent milling step, substantially for adjusting the superstructure 200.

The dental bridge intermediary structure 20 may then be made by zirconiumdioxide ($ZrO_2$), through a milling/cutting process, such as CNC cutting, which will be described below.

However, it will be appreciated by a person skilled in the art that the dental bridge intermediary structure 20 may also be sintered or milled from plastics. Such plastic structures would be suitable for use as temporary bridges, after an optional application of a facing material thereon. An advantage with this is that the structure cost less to produce, and the patient would receive a temporary bridge, while the permanent bridge was manufactured. Temporary bridges in plastic material would be advantageous, since exact adjustment with regard to implant positions and angles could be compensated for by the flexibility in the plastic material.

In an embodiment, the dental bridge intermediary structure is made from plastic material by three dimensional printing, which is well known to a person skilled in the art and will thus not be further described.

In a specific embodiment, the dental bridge intermediary structure 20 is cast or molded. The connection piece 210 may be cast in the same process as the superstructure 200, in the same piece as the superstructure. In this way, the superstructure 200 is obtained with integrated connection piece 210. The connection piece 210 is thus homogenous with the superstructure 200.

The casting may be made according to methods known to a person skilled in the art. For example, a plastic model, such as a plastic burnout model of the dental bridge intermediary structure 20, may be manufactured. Based on the model, a mould may be manufactured and the casting subsequently performed, as is well known to a person skilled in the art.

In an embodiment, part of the dental bridge intermediary structure 20 is cast and part of the dental bridge intermediary structure 20 is sintered. The different parts are then attached to each other by a suitable method, such as welding, before the dental bridge intermediary structure 20 is milled.

An advantage with this is that the different pieces may be manufactured separately which may be cost effective.

In a specific embodiment, the connection piece 210 is cast and the superstructure 200 is sintered. The connection piece 210 and the superstructure 200 are then welded together to form the dental bridge intermediary structure 20.

The connection means 220 comprised in the connection piece 210 may be cavities, such as holes, for connecting the dental bridge intermediary structure 20 to a cutter. It may also be indentions, corresponding to gripping teeth in a holding device on the cutter or a shape having its correspondence on the cutter, as long as the connection piece 210 may guarantee that the position of a certain set of reference coordinates may be transferred from the sintering step to the milling/cutting, such that the milling/cutting unit will know where the cutting/milling action is to be performed to shape and smoothen dental implant connections on the superstructure. This is obtained by the reference means 230.

In a specific embodiment the connection means 220 for connecting the dental bridge intermediary structure 20 to a mill/cutter are holes in the plate, which allow locking means, such as screws, bolts, pins, pegs etc., to be applied in the holes to subsequently lock the dental bridge intermediary structure 20 to the mill/cutter.

An advantage with this is that the dental bridge intermediary structure 20 may be held securely in place by the connection piece. This allows the dental bridge intermediary structure 20 to be cut by an industrial cutter, such as a computed numerically controlled (CNC) cutter.

In an embodiment, the connection piece 210 is directly fastened in the cutter, thus holding the dental bridge intermediary structure 20 in position for the cutting process. The fastening may be made by means of a conventional chuck, or by any other means as allowed by the machine.

An advantage is that the reference means 230 for positioning of the superstructure 200 may be positioned on the connection piece 210, such that the reference means 230 makes it possible to read or interpret the position of the connection piece 210 and thereby the position of the dental bridge intermediary structure 20. Thus, it is possible to establish and translate the coordinates of the specific parts of the dental bridge superstructure, when moving the product from the sintering step to the cutting or milling step. Specifically, this is possibly since the reference is no longer dependent on boundaries or edges of the sintered superstructure. Instead, both the drawing and dental bridge intermediary structure 20 has specific reference means for this purpose.

In a specific embodiment, the reference means 230 are holes in the plate. In another specific embodiment, the reference means 230 are protrusions from the plate.

In an embodiment, the dental bridge intermediary structure 20 is automatically positioned in the cutter, based on the location of the connection piece 210 and the superstructure 200.

The reference means 230 may form a pattern, recognizable by a CNC cutter as the reference or zero position, from which the CNC cutter can navigate around the edges of the dental bridge intermediary structure 20. The reference means 230, such as holes or protrusions, are thus code points, occurring both in the drawing of the dental bridge intermediary structure 20 and in the actual dental bridge intermediary structure 20.

An advantage with this is that it allows for automated cutting, since it is possible for the CNC cutter to orient the dental bridge intermediary structure 20 in relation to the Computer-aided design (CAD)/Computer-aided manufacturing (CAM) drawings and thus exactly perform the cutting process. This may be achieved by the CNC cutter recognizing the pattern and correlating the pattern to the CAD/CAM drawing, which in turn gives the CNC cutter automatic guiding about where to cut the dental bridge intermediary structure 20 by providing a common reference between the drawing and the structure, since connection piece 210, and thus the reference means 230, and the dental bridge intermediary structure 20 are made in the same integral and homogenous piece from the same drawing. Thus, a cut product with a high level of detail may be obtained from a sintered structure, without the need of manual adaptation of the dental bridge intermediary structures 20 position in the cutter.

Figure 3:
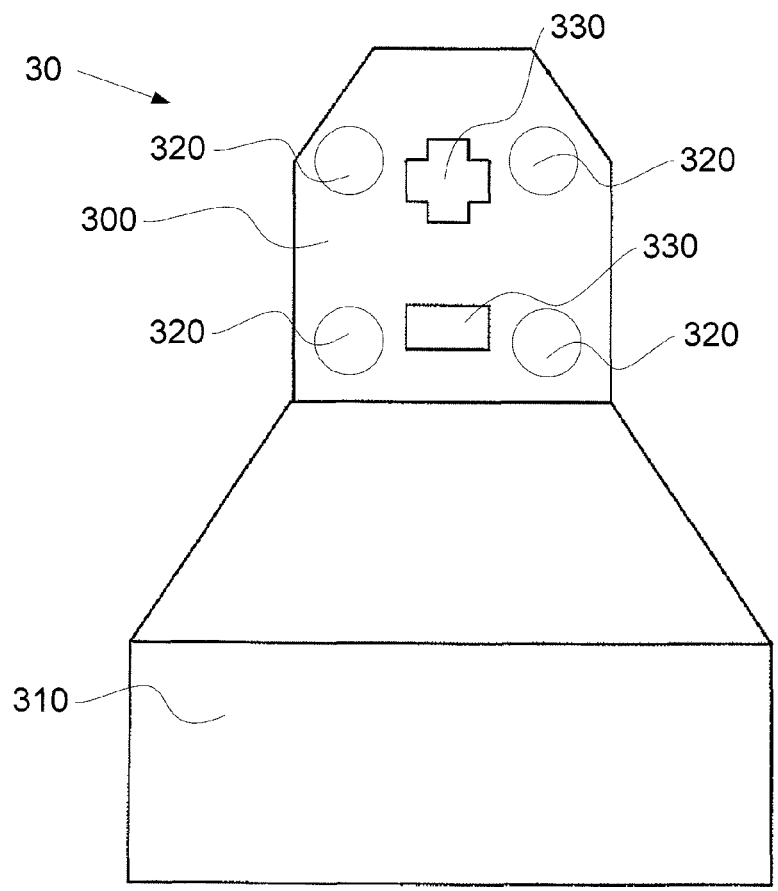
FIG. 3 is an illustration of a connection piece according to an embodiment.

In an embodiment according to FIG. 3, a mill/cutter reference piece 30 for a dental bridge intermediary structure 20 is provided. The mill/cutter reference piece 30 is adapted to be positioned, such as mounted, on a mill/cutter, such as a CNC cutter, for receiving thereon a connection piece, such as the connection piece 210 illustrated in FIG. 2. The mill/cutter reference piece 30 comprises a positioning portion 300 and a fastening portion 310. The positioning portion 300 comprises complimentary connection means 320 for interaction with the connection means 220, comprised on the connection piece 210, of a dental bridge intermediary structure 20. When superimposed, the complimentary connection means 320 and the connection means 220 of the connection piece 210 interact to securely position the dental bridge intermediary structure 20 to the mill/cutter reference piece 30. By fastening the fastening portion 310 of the mill/cutter reference piece 30 to a machine, such as a CNC cutter, the dental bridge intermediary structure 20 and consequently the superstructure 200 are fastened to the machine. The fastening may be made by means of a conventional chuck, or by any other means as allowed by the machine.

In an embodiment, the complimentary connection means 320 of the mill/cutter reference piece 30 is protrusions and the connection means 220 of the connection piece 210 is holes. Thus, in an x-y-z coordinate system, when the holes are superimposed on the protrusions in the z direction, the dental bridge intermediary structure 20 will be held in place with respect to the mill/cutter reference piece in x and y directions.

The mill/cutter reference piece 30 further comprises complimentary reference means 330 for interaction with the reference means 230 of a dental bridge intermediary structure 20. The reference means 230 on the connection piece 210 may for example comprise at least one female part, such as hole/holes, corresponding to reference means 330 on the mill/cutter reference piece 30 in form of at least one male part, such as pin/pins. When superimposed, complimentary reference means 330 interact with the reference means 230 to give a reference point, such as a zero point, for the dental bridge intermediary structure 20 and the mill/cutter reference piece 30 combined. The complimentary connection means may be protrusions, such as geometrical shapes recognizable by a CNC cutter. The reference means 230, 330 facilitate assurance of correct positioning of the connection piece 210 on the miller/cutter, since for example male/female connection may assure secure placement of the connection piece 210, and thus the superstructure 20, on the mill/cutter, allowing for easy attachment of the connection piece 210 to the mill/cutter by aid of separate securing means, such as screws or bolts. Another advantage is that it is possible to read or interpret the position of the dental bridge intermediary structure 20 in relation to the mill/cutter reference piece 30.

In an embodiment, the dental bridge intermediary structure 20 is attached to the connection piece 210 by connectors or cross-links 240, such as pegs, extending between the connection piece 210, such as a plate, and the superstructure 200. In a specific embodiment the connection piece 210, the connectors 240 and the superstructure 200 are sintered in the same process and in the same piece. The connectors or cross-links 240 may be arranged such that they are substantially evenly distributed along the extension of the superstructure 200. A first advantage with this is that the connectors 240 and the connection piece 210 stabilize the superstructure 200 during sintering, to prevent or counteract warping of the superstructure 200. A second advantage is that it is easy to separate the dental bridge intermediary structure 20 from the connection piece 210 by simply cutting the connectors or cross-links 240, once the cutting process is complete.

In an embodiment, the reference means 230 or the connection means 220 are holes extending through the connection piece 210.

Preferably, both the reference means 230 and the complimentary reference means 330 are accessible when the dental bridge intermediary structure 20 and the connection piece are connected. An advantage with this is that the CNC cutter has two sets of reference points, which improves robustness.

Figure 4:
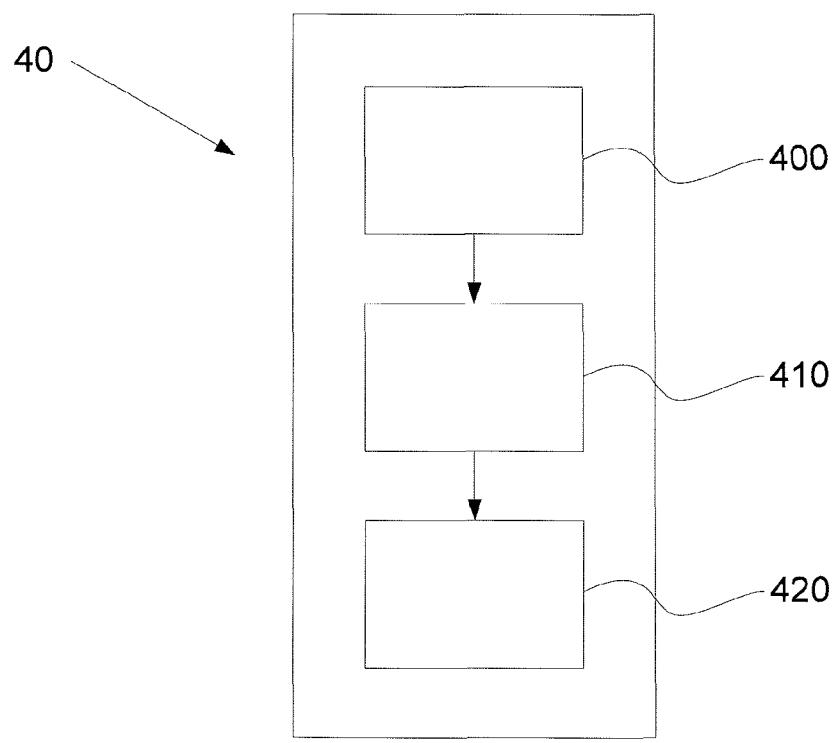
FIG. 4 is an illustration of a method according to an embodiment.

In an embodiment according to FIG. 4, a method 40 for producing a dental bridge intermediary structure is provided. The method 40 comprises a step of shaping 400, such as sintering, casting, milling or a combination of sintering and casting, a dental bridge intermediary structure comprising a superstructure 200 and a connection piece 210, wherein the connection piece 210 comprises connection means 220 for connecting the dental bridge intermediary structure 20 to a cutter, and reference means 230 for positioning of the superstructure 200 in the cutter. The reference means 230 and the connection means 220 may be the same structural unit, such as the same holes.

The sintering may be performed with a device according to FIG. 1, or any other sintering device known to a person skilled in the art. The casting may be performed according to any suitable method, which will be appreciated by a person skilled in the art. The milling may be performed according to any suitable method, such as CNC cutting.

If the shaping 400 comprises casting, the shaping 400 step may optionally include producing a model, such as a plastic model, for subsequent production of a mould and casting.

An advantage with this is that the model may be produced on demand, by simple means, and sent to a separate location for casting.

If a combination of sintering and casting is utilized, the sintered and cast parts may be attached by any suitable method known to a person skilled in the art, such as welding.

Before the sintering, a dental technician supplies an original of the desired bridge superstructure, and a model of the shape of a patient jaw, including the position of the dental implants. The original is scanned according to methods known to a person skilled in the art, to obtain a computer rendering or drawing of its shape. The model is also scanned, to obtain a computer rendering or drawing of the position of the respective implants. Based on these computer renderings or drawings, a CAD/CAM software is used to design a computer rendering or drawing of the dental bridge superstructure 200.

Based on the computer rendering or drawing, a standard laser sintering device is sintering a metal powder, such as powdered CoCr, into a three dimensional dental bridge intermediary structure 20 comprising a superstructure 200 and a connection piece 210, wherein the connection piece 210 comprises connection means 220 for connecting the dental bridge intermediary structure 20 to a cutter, and reference means 230 for positioning of the superstructure 200 in the cutter. The sintered dental bridge intermediary structure 20 may be heated after the sintering step to relieve tension that may be the result of the sintering process, which is well known to a person skilled in the art.

During this process, the connection piece 210 may serve as a support for the superstructure, to prevent or counteract warping of the superstructure 200, while simultaneously providing for coordinate translation between the sintering and the milling/cutting.

Next, the method comprises a step of connecting 410 the unit to a machine cutter, such as a CNC cutter. This makes it possible to cut the dental bridge intermediary structure 20 to obtain a high finish of the structure, and especially of the seats for connection to the dental implants. Thus, the seats for connection to the dental implants are cut with a cutter subsequently of the sintering step. In connection to the cutting of the seats screw channels may be cut. Cutting the screw channels after the sintering process allows for more precise screw channel geometry, since the screw channels are cut after the structure has warped and stabilized. Thus, the screw channels may be cut in a precise geometry, such as straight screw channels, or bent or angled screw channels, if one wishes to position the mouth of the screw channel on the buccal side of the dental bridge intermediary structure 20. The connecting may be obtained by a chuck, clamp or other suitable device as known to a skilled person.

The cutting 420 may be guided by reference means located on the connection piece 210. This is advantageous because the cutter, such as a CNC cutter, may easily find the cutting surfaces, i.e. edges of boundaries on the dental bridge intermediary structure 20, by correlating these to the position of the reference means 230 and specifically cut the structure according to the CAD/CAM rendering. Since the whole dental bridge intermediary structure 20 is part of the CAD/CAM rendering, all the coordinates are easily accessible to the CNC cutter, as known to a person skilled in the art.

In a specific embodiment, where the connection piece is a plate, the guiding means are holes. The position of the holes on the plate is the same as in the drawing. Thus, the holes provide a common reference between the drawing and the structure. Since the CNC cutter is guided by the CAD/CAM rendering, as known to a person skilled in the art, the CNC cutter may thus cut the dental bridge intermediary structure 20 based on the position of the holes in the connection piece.

The method 40 further comprises a step of cutting 420 the dental bridge intermediary structure with a cutter, guided by reference means 230 located on the connection piece 210. The cutter may be any cutter, such as a CNC cutter, guided by CAD/CAM software and the reference means.

Since the cutter is guided by the same CAD/CAM rendering as the sintering machine, the cutter will only cut the parts of the surface of the dental bridge intermediary structure resulting from imperfections in the sintering process, which reduces waste. Especially important is to obtain precise seats for fastening the superstructure to the dental implants of the patient.

Since the cutter is guided by the reference means 230, no manual adjustment is needed to position the dental bridge intermediary structure 20 in the cutter.

In an embodiment, the reference means 230 are protrusions in shape of a "+"-sign and a "−"-sign. The reference means 230 marks the zero value for the cutter in relation to the rest of the dental bridge intermediary structure 20.

The method 40 further comprises a step of separating 430 the superstructure from the connection piece 210 to obtain a dental bridge superstructure 200.

Figure 5:
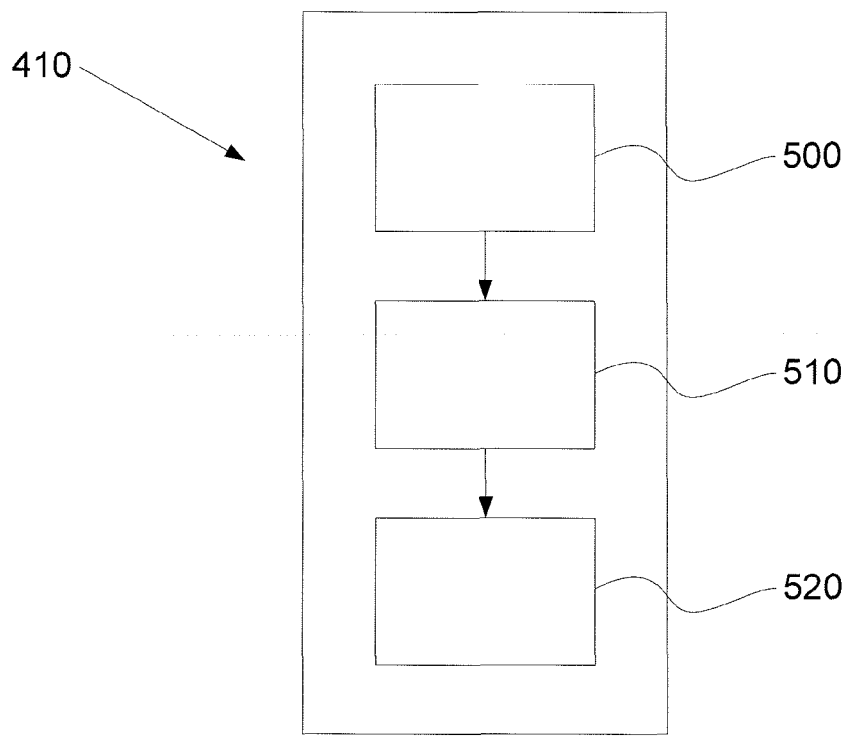
FIG. 5 is an illustration of a method according to an embodiment.

In an embodiment according to FIG. 5, the connection step 410 is done by means of a connection piece and comprises a step of fastening 500 a fastening portion 310 of a mill/cutter reference piece 30 to the cutter. The fastening may be by means of a conventional chuck, or by any other means as allowed by the machine.

Next, the connection step 410 comprises a step of superimposing 510 complimentary connection means 320 of the reference piece 30 upon the connection means 220.

In an embodiment, the complimentary connection means 320 are protrusions and the connection means 220 are holes. In an x-y-z coordinate system, when the holes are superimposed on the protrusions in the z-direction, the protrusions engage the holes and secure the dental bridge intermediary structure 20 to the reference piece 30 in the x-y-direction. The dental bridge intermediary structure 20 may subsequently be locked to reference piece 30 in the z-direction by a clamp, shackle etc.

An advantage with this is that the dental bridge intermediary structure 20 may be easily dislocated from the cutter, to allow comparison with the model, and subsequently easily relocated in the cutter, to continue the cutting process.

In an embodiment, both the complimentary connection means 320 and the connection means 220 are holes. In an x-y-z coordinate system, when the holes are superimposed on the protrusions in the z-direction, the result is a hole throughout both the dental bridge intermediary structure 20 and the reference piece 30 in the z-direction. Locking means, such as screws, bolts, pins, pegs etc., may then be applied in the superimposed holes to subsequently lock the dental bridge intermediary structure 20 to reference piece 30 in the x-y-z-direction.

An advantage with this is that the dental bridge intermediary structure 20 may be easily dislocated from the cutter, to allow comparison with the model, and subsequently easily relocated in the cutter, to continue the cutting process.

Next, the connection step 410 comprises a step of superimposing 520 complimentary reference means 330 of the reference piece 30 upon the reference means 230.

In an embodiment, the cutting 420 is guided by the same CAD/CAM rendering as the shaping 400.

An advantage with this is that it is easy for the cutter to find the boundaries of the dental bridge superstructure 200 automatically, i.e. without manual measuring or calibration. Thus, the cutting step is faster and results in less waste material.

Since the reference means are present in the CAD/CAM rendering of the dental bridge intermediary structure 20, which is guiding the cutter, such as a CNC cutter, the cutter will find the boundaries of the dental bridge superstructure 200 automatically, i.e. without manual measuring or calibration.

In an embodiment, the complimentary reference means 330 are protrusions and the reference means 230 are holes. In an x-y-z coordinate system, when the holes are superimposed on the protrusions in the z-direction, the protrusions engage the holes and extend through the holes. This makes the complimentary reference means 330 accessible for detection by the cutter, as is appreciated by a person skilled in the art.

Since the reference means are present in the CAD/CAM rendering of the dental bridge intermediary structure 20 and the mill/cutter reference piece 30, which is guiding the cutter, such as a CNC cutter, the cutter will find the boundaries of the dental bridge superstructure 200 automatically, i.e. without manual measuring or calibration.

In an embodiment, a dental bridge superstructure 200 is provided, said dental bridge superstructure being obtainable by a method as described above.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method for producing a dental bridge superstructure, said dental bridge superstructure comprising seats for connection to dental implants, comprising the steps of:
   shaping a dental bridge intermediary structure, said dental bridge intermediary structure comprising a superstructure and a connection piece, wherein the connection piece comprises means for connecting the dental bridge intermediary structure to a cutter, and reference means for positioning of the superstructure in the cutter;
   connecting the connection piece to the cutter;
   cutting said seats for connection to dental implants with the cutter.

2. The method according to claim 1, wherein said dental bridge superstructure comprising screw channels for screw retention of the superstructure to dental implants, the method further comprising cutting said screw channels.

3. The method according to claim 1, further comprising separating the superstructure and the connection piece.

4. The method according to claim 1, wherein the connecting comprises
   fastening a fastening portion of a reference piece to the cutter;
   superimposing complimentary connection means of the reference piece upon the connection means; and
   superimposing complimentary reference means of the reference piece upon the reference means.

5. The method according to claim 4, further comprising the step of locking the superimposed complimentary connection means to the connection means.

6. The method according to claim 1, wherein the cutting is guided by the same CAD/CAM rendering as the shaping.

7. The method according to claim 1, wherein the shaping is done by sintering, casting, milling, or any combination of two or more from the group consisting of sintering, casting, and milling.

* * * * *